United States Patent [19]

Larson

[11] Patent Number: 4,623,338
[45] Date of Patent: Nov. 18, 1986

[54] LINE CLAMP FOR AN OSTOMY BAG

[76] Inventor: Robert Larson, 475 Green Bay Rd., Cedarburg, Wis. 53012

[21] Appl. No.: 792,016

[22] Filed: Oct. 28, 1985

[51] Int. Cl.[4] ............................................. A61F 5/44
[52] U.S. Cl. ................................ 604/339; 24/135 N
[58] Field of Search ............................ 604/338-343, 604/33, 34, 902; 251/7, 8; 128/346; 24/115 G, 115 H, 135 N

[56] References Cited

U.S. PATENT DOCUMENTS 3,268,965  8/1966  Arthur .............................. 24/135 N

FOREIGN PATENT DOCUMENTS 623406  12/1935  Fed. Rep. of Germany ... 24/135 N
48032   2/1940   Netherlands ..................... 24/135 N Primary Examiner—Stephen C. Pellegrino
Assistant Examiner—J. L. Kruter
Attorney, Agent, or Firm—Bayard H. Michael

[57] ABSTRACT

The clamp has an elongated body with a transverse bore which is intersected on an axial threaded hole originating at one end of the body. A transverse slot originating closer to the one end of the body tangentially intersects the bore closer to the one end of the body. A screw is threaded into the hole from the one end and bears on elastic lines (or cords) and tends to push them into the hole. When used with a colostomy pouch the clamp holds the usual retaining bead tight against the pouch connector and plate flange.

1 Claim, 6 Drawing Figures

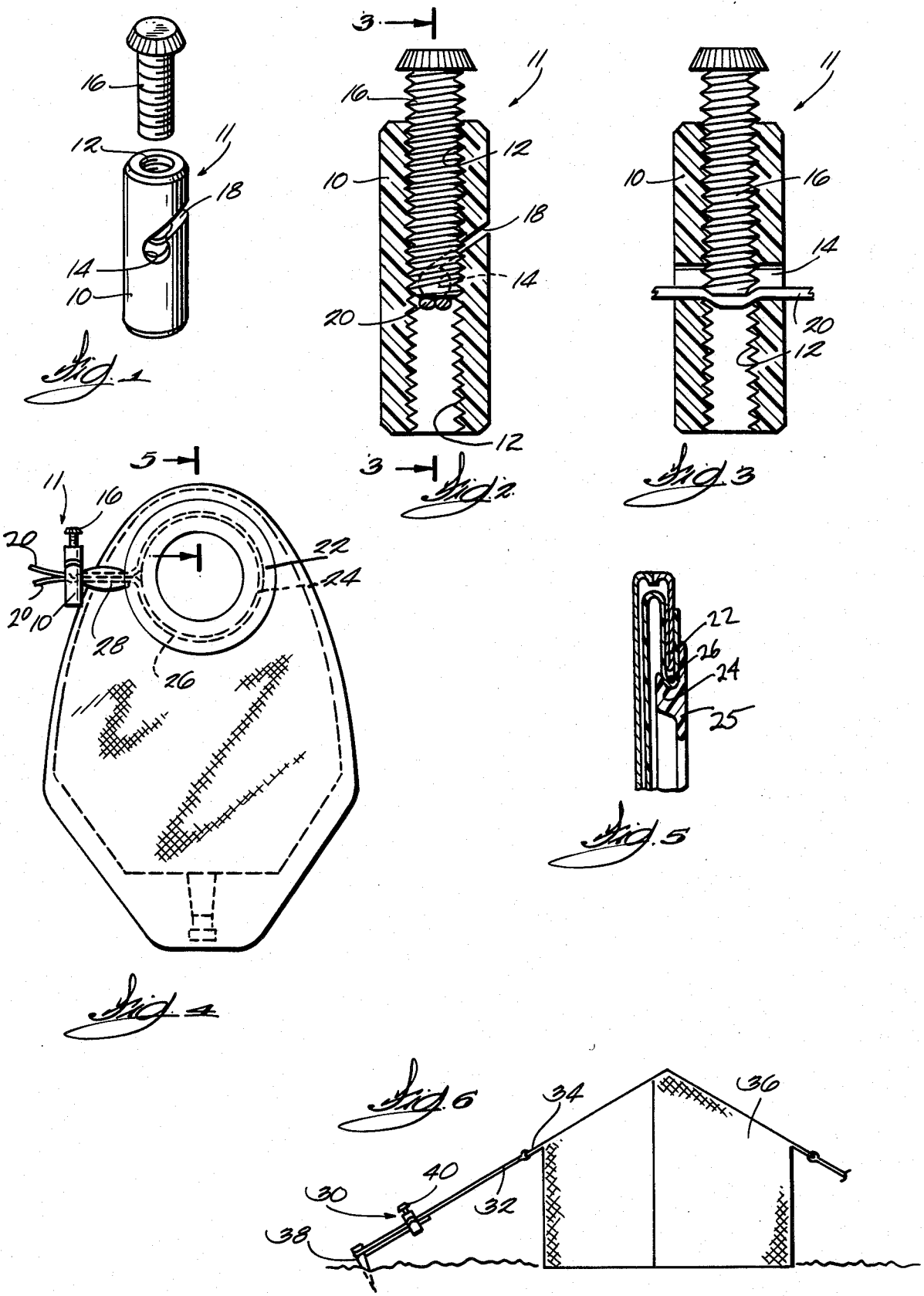

LINE CLAMP FOR AN OSTOMY BAG

BACKGROUND OF THE INVENTION

This invention is the result of difficulties with suitably clamping or restraining elastic cords used in securing the tubular opening of an ostomy pouch on the mounting flange of the face plate worn by a patient around the stoma. The elastic cord is to secure the pouch on the plate. The ends of the cord are pulled through a bead which is pushed up to the flange. In theory, the bead grips the cord tight enough to prevent loss of grip on the pouch. In fact, the elastic cord slowly pulls through the bead and the grip is lost; the contents leak and the patient suffers a loss of dignity.

It became apparent that the usual method of obtaining a reasonably fast grip on the elastic cord is unsatisfactory.

The object of this invention is to provide a clamp which can positively secure the elastic cord and prevent slipage and loss of grip on the cord.

SUMMARY OF THE INVENTION

This invention provides an elongated body having a transverse bore which is intersected by an axial hole originating at one end of the member and which extends past the bore. The body also has a transverse slot originating closer to the one end of the body and tangentially intersecting the bore closer to the one end of the body. A screw is threaded into the hole and extends into the bore to bear against cords extending through the bore.

In practice, this screw tends to force the cords into the hole on the side of the bore opposite the side through which the screw projects. This obtains a sharp pinching action as it tends to push the cord into the hole. Thus, the grip on the cord is not simply compression, but it is also a pinching action which appears to preclude the flowing type of slippage characteristic of elastic cords.

The invention also contemplates the novel use of such a clamp in conjunction with the bead heretofore used in clamping the ostomy pouch to the face plate. Thus, the bead is moved up to the flange and then the clamp is secured on the side of the bead opposite the end of the bead facing the flange. The bead has two functions in this instance; one is to temporarily secure the elastic and the other is position the clamp far enough from the flange so that the screw on the clamp can be opperated easily with minimum interference from the proximity of the flange.

BRIEF DESCRIPTION OF THE DRAWINGS

FIG. 1 is a perspective view of the clamp.
FIG. 2 is a vertical section through the clamp.
FIG. 3 is a vertical section as shown by section lines 3—3 in FIG. 2.
FIG. 4 is a view showing the elastic cord wrapped around the neck of the ostomy pouch and the flange and shows the bead and clamp in position.
FIG. 5 is a section taken on line 5—5 in FIG. 4.
FIG. 6 shows use of this device as a line clamp in conjunction with a tent.

DETAILED DESCRIPTION OF THE DRAWINGS

The line clamp has an elongated body or tube 10 having an axial bore or hole 12 therein. The hole extends through the body, i.e., it extends past the transverse bore 14 and is threaded to receive screw 16. There is a transverse slot 18 in the body which originates closer to one end (the upper end in the drawings) than to the other end of the body and extends into the body to tangentially intersect the transverse bore 14 at the side or portion of the bore closer to the one end of the body. Hole 12 has a greater diameter than the transverse bore 18. Therefore, when elastic lines 20—20 are positioned in the transverse bore the end of the screw 16 will bear on the lines and tend to stuff them into the hole 12 on the opposite side of the bore. This causes the line to not only be squeezed into the bore, but also to be pinched against the corners of the intersection of the bore and the hole. This effectively precludes any movement of the cords. Normally, an elastic cord is very difficult to work with because it tends to "flow" past a clamp or the like.

Since the axial hole 12 is threaded throughout its length, the clamp can be provided with another screw threaded in from the opposite end and also bear against and further clamp the lines.

It will be appreciated that the same type of construction can be utilized to clamp wires or rope. The term "lines" is, therefore, used to embrace elastic cord, string, wire, rope or any similar material. This invention is not limited by way of size. The original device was designed to grip elastic cord approximately 1/16" thick. It can clamp any desired dimension.

FIG. 4 shows, in general terms, the neck fitting 22 of an ostomy pouch fitting over the flange 24 of face plate 25 with an elastic cord 26 wrapped around the neck fitting. The ends of the cord run through the central opening in the bead 28 which is moved up tight against the flange 24. In theory this has enough frictional engagement with the cord to prevent slipping. In fact, it doesn't prevent slippage. The present clamp 11 is mounted on the side of the bead away from the surgical appliance (ostomy pouch and fitting). This gets the clamp far enough away from the appliance so the user's fingers can easily work the screw without interference from the appliance. The bead also functions to temporarily hold the elastic cord in position while the clamp is mounted and tightened.

In FIG. 6, a larger version of the clamp is used as a line clamp for a tensioning line on a tent. Thus, the clamp 30 grips both runs of the tension line 32 running from the eve 34 of tent 36 to the stake 38 and back up the line a little bit where the bitter end of the line is also lead through the clamp. The clamp (similar to that described above, having a handle-type screw 40) is tightened to secure the line and maintain tension. With this simple arrangement, the tension in the rope 32 can be adjusted from time to time to accommodate changes in the tightness of the tent cloth caused by rain or sunshine.

As indicated, there are other situations where a clamp of this type can be used. The clamp is not limited to use with elastic cord although use with elastic cord is indeed a very difficult usage and the clamp works very well in that use.

I claim:
1. Surgical apparatus comprising,
  a colostomy plate fitting having an annular mounting flange,
  a colostomy pouch having a neck fitting over said flange, an elastic cord, having terminal ends wrapped around said neck to hold it on said flange, a bead having a through-bore, the ends of said cord passing through said bore and said bead being substantially adjacent said flange, a clamp including an elongated body, a transverse bore in said body, an axial hole originating at one end of said body and extending past said bore, a transverse slot in said body originating closer to said one end and tangentially intersecting said bore closer to said one end, and a screw threaded into said hole and extending into said bore, said cord ends being positioned in said bore of said clamp, said clamp being positioned next to said bead, and said screw being turned down on said ends.

* * * * *